US010247783B2

(12) United States Patent
Mensah-Brown

(10) Patent No.: US 10,247,783 B2
(45) Date of Patent: Apr. 2, 2019

(54) SENSOR SYSTEM FOR MEASURING BATTERY INTERNAL STATE

(71) Applicant: Ford Global Technologies, LLC, Dearborn, MI (US)

(72) Inventor: Arnold Kweku Mensah-Brown, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 14/494,137

(22) Filed: Sep. 23, 2014

(65) Prior Publication Data

US 2016/0084911 A1    Mar. 24, 2016

(51) Int. Cl.
*B60L 11/14* (2006.01)
*B60L 11/16* (2006.01)
(Continued)

(52) U.S. Cl.
CPC ...... *G01R 31/3606* (2013.01); *B60L 11/1803* (2013.01); *B60L 11/1861* (2013.01); *G01K 17/00* (2013.01); *G01N 29/022* (2013.01); *G01N 29/024* (2013.01); *G01N 29/04* (2013.01); *G01R 31/3648* (2013.01); *G01R 31/3679* (2013.01); *G01N 2291/012* (2013.01); *G01N 2291/02863* (2013.01); *G01N 2291/02881* (2013.01);
(Continued)

(58) Field of Classification Search
CPC ............................ B60R 21/013; B60R 16/037
See application file for complete search history.

(56) References Cited

U.S. PATENT DOCUMENTS 4,865,931 A * 9/1989 McCullough, Jr. ..... D01F 9/155
429/338
5,786,040 A    7/1998 Leddy et al.
(Continued)

FOREIGN PATENT DOCUMENTS

CN    1194614 A    9/1998

OTHER PUBLICATIONS

Buchmann, Cadex Electronics, Inc., 9-1-1 Magazine, Jan. 20, 2012, Battery Fuel Gauge: Factual or Fallacy? (4 pages).
(Continued)

*Primary Examiner* — Bickey Dhakal
*Assistant Examiner* — Charles S Laughlin
(74) *Attorney, Agent, or Firm* — David B. Kelley; Brooks Kushman P.C.

(57) ABSTRACT

Systems and methods for sensing internal states of vehicle batteries are described. From this internal state information, various physical characteristics of the battery can be measured, calculated or inferred. A vehicle can include an electric motor, a battery to store electrical energy for the electric motor, and a sensor connected to the battery to sense a battery state, to receive an input signal, and to wirelessly transmit an output signal indicating the battery state. The vehicle can also include control circuitry to receive the output signal and to control the electric motor and the battery. In examples, the battery may have a physical property that changes based on a state of the battery. This physical property may be measured by the sensor. The sensor may be passive and built into the structure of the battery. The sensor can be a magnetic field sensor or a surface wave acoustic sensor.

11 Claims, 10 Drawing Sheets

(51) Int. Cl.
*B60L 7/12* (2006.01)
*G01R 31/36* (2019.01)
*B60L 11/18* (2006.01)
*G01K 17/00* (2006.01)
*G01N 29/04* (2006.01)
*G01N 29/02* (2006.01)
*G01N 29/024* (2006.01)

(52) U.S. Cl.
CPC .......... *G01N 2291/045* (2013.01); *G01N 2291/0423* (2013.01); *Y02T 10/7005* (2013.01); *Y02T 10/705* (2013.01); *Y02T 10/7044* (2013.01); *Y10S 903/907* (2013.01); *Y10S 903/93* (2013.01)

(56) References Cited

U.S. PATENT DOCUMENTS

| | | | |
|---|---|---|---|
| 5,928,804 A | 7/1999 | Leddy et al. | |
| 6,184,656 B1* | 2/2001 | Karunasiri | B60L 3/0046 180/65.8 |
| 6,479,176 B2 | 11/2002 | Leddy et al. | |
| 7,417,405 B2* | 8/2008 | Carrier | H02J 7/0021 320/116 |
| 7,425,816 B2 | 9/2008 | Meyer et al. | |
| 7,500,379 B2 | 3/2009 | Hines | |
| 7,623,037 B1 | 11/2009 | Malocha | |
| 7,633,206 B2 | 12/2009 | Andle et al. | |
| 7,642,898 B1 | 1/2010 | Malocha et al. | |
| 7,777,625 B1 | 8/2010 | Puccio et al. | |
| 7,791,249 B2 | 9/2010 | Hines et al. | |
| 7,825,805 B2 | 11/2010 | Malocha et al. | |
| 7,915,785 B2 | 3/2011 | Andle et al. | |
| 7,928,690 B2 | 4/2011 | Koch et al. | |
| 7,936,151 B2 | 5/2011 | Bueur et al. | |
| 7,944,181 B2 | 5/2011 | Johnson et al. | |
| 7,952,482 B2 | 5/2011 | Malocha et al. | |
| 7,961,105 B2 | 6/2011 | Puccio et al. | |
| 8,108,160 B2 | 1/2012 | Liu et al. | |
| 8,169,320 B2 | 5/2012 | Malocha et al. | |
| 8,198,864 B2 | 6/2012 | Koch et al. | |
| 8,278,876 B2 | 10/2012 | Bueur et al. | |
| 8,384,524 B2 | 2/2013 | Cobianu et al. | |
| 8,817,428 B2 | 8/2014 | Perez et al. | |
| 8,994,370 B2 | 3/2015 | Pannetier-Lecoeur et al. | |
| 2009/0115420 A1 | 5/2009 | Koch et al. | |
| 2010/0079145 A1* | 4/2010 | Meisner | B60L 11/1851 324/432 |
| 2010/0227222 A1 | 9/2010 | Chang et al. | |
| 2012/0086457 A1 | 4/2012 | Meisner et al. | |
| 2012/0089299 A1* | 4/2012 | Breed | B60C 11/24 701/36 |
| 2012/0161776 A1* | 6/2012 | Koch | G01R 31/3606 324/426 |
| 2012/0316814 A1* | 12/2012 | Rahaman | G01R 31/3679 702/63 |
| 2013/0057288 A1 | 3/2013 | Ogata et al. | |
| 2013/0149565 A1 | 6/2013 | Conell et al. | |
| 2013/0151180 A1* | 6/2013 | Koch | B60L 11/1805 702/63 |
| 2013/0187645 A1* | 7/2013 | Pannetier-Lecoeur | G01R 15/205 324/252 |
| 2014/0297084 A1 | 10/2014 | Meisner et al. | |

OTHER PUBLICATIONS

Chernova, N. A., et al., "What can we learn about battery materials from their magnetic properties?," J. Mater. Chem., 2011, pp. 9865-9875, vol. 22.

Fisher, B., "Surface Acoustic Wave (SAW) Cryogenic Liquid and Hydrogen Gas Sensors," 2012, 259 pgs., Doctoral Dissertation.

Humphries, J., "Passive, Wireless SAW OFC Strain Sensor and Software Defined Radio Interrogator," Frequency Oontrol Symposium (FCS), 2012, 146 pgs., 2012 IEEE International.

Malocha, D.C., "Surface Acoustic Wave (SAW) Wireless Passive RF Sensor Systems," http://www.slideshare.net/fuentek/surface-acoustic-wave-saw-wireless-passive-rf-sensor-systems (accessed Oct. 18, 2012), 75 pgs.

Malocha, D. C. et al., "Orthogonal Frequency Coding for SAW Device Applications," Proceedings of the IEEE Ultrasonics Symposium, 2004, 4 pgs.

RFSAW, Inc., "The Global SAW Tag—A New Technical Approach," RFSAW, Richardson, 2004, 4 pgs.

Tinnemeyer, J., "New Advances in Lithium Ion Battery Monitoring," 2012, 9 pgs.

Wilson, W. C. et al., "Rapid SAW Sensor Development Tools," CANEUS/NASA Workshop on Fly-by-Wireless for Aerospace Vehicles, Jan. 1, 2007, 7 pgs., Grapevine, TX.

\* cited by examiner

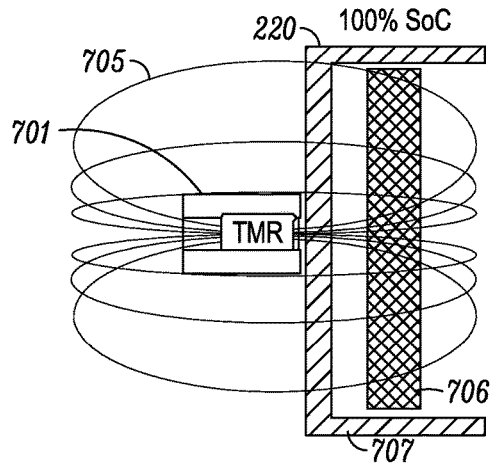
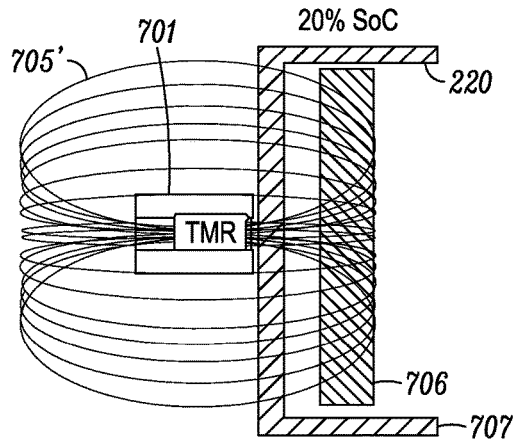
*FIG. 7A*  *FIG. 7B*
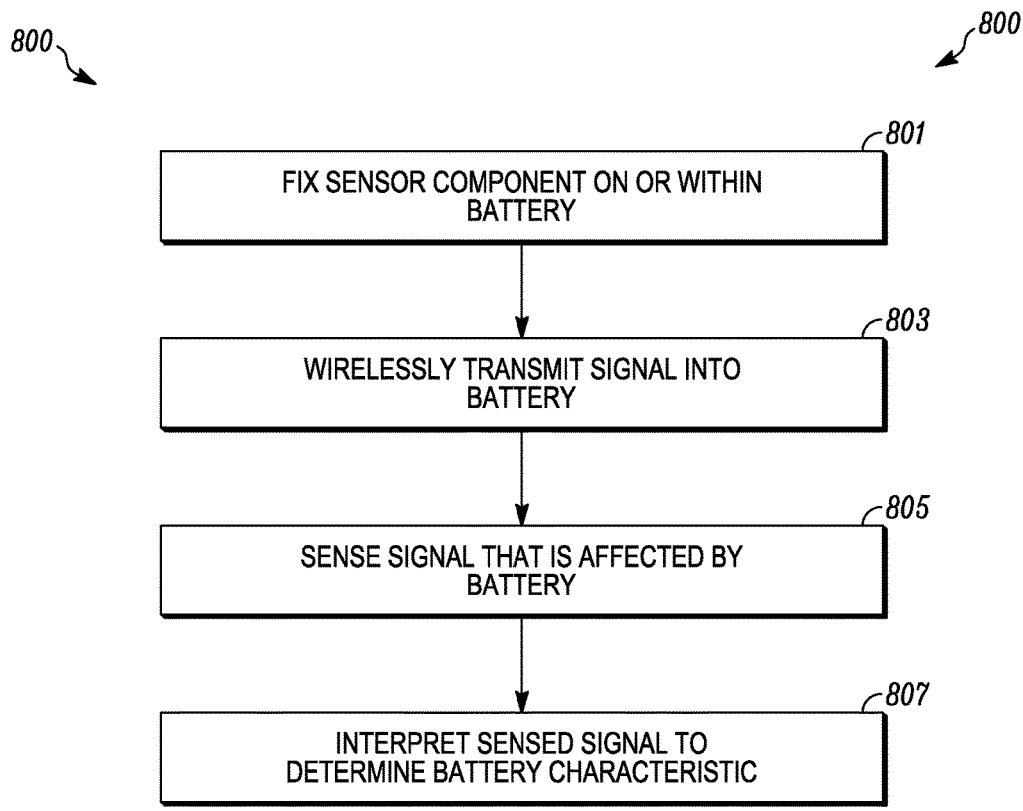
*FIG. 8*

SENSOR SYSTEM FOR MEASURING BATTERY INTERNAL STATE

TECHNICAL FIELD

Various embodiments relate to systems and methods for sensing a battery state, and a vehicle using such systems and methods.

BACKGROUND

Batteries used in vehicles may be monitored using various sensors to determine physical properties of the battery. Temperature of a battery can be approximated by a thermistor on the bus bar attached to a battery. Battery cell voltage can be measured using a chip that may be multiplexed to a plurality of battery cells, connected with physical wiring, and drawing electrical power from the battery cell itself. Current measurement can be done using a Hall Effect current sensor that generates a difference in electric potential across the sides of a current-carrying conductor that is connected to the battery. As there is a desire to increase efficiency of vehicles powered by batteries, improved data regarding battery physical state may result in improved performance.

SUMMARY

Systems and methods for sensing the internal states of batteries for vehicles are described. From this internal state information, various physical characteristics of the batteries can be measured, calculated or inferred.

An electric vehicle, e.g., an HEV, can include an electric motor, a battery to store electrical energy for the electric motor, and a sensor connected to the battery to sense a battery state, to receive an input signal, and to wirelessly transmit an output signal indicating the battery state, and control circuitry to receive the output signal and to control the electric motor and the battery. In certain examples, the battery may have a physical property that changes based on a state of the battery. This physical property may be measured by the sensor. The sensor may be passive and built into the structure of the battery.

In an example, the sensor is a passive radio frequency identification tag. The battery includes an electrode that has a Young's modulus that changes based on battery state, and the passive radio frequency identification tag changes its output signal based on a change in the Young's modulus. The control circuitry uses a change in the output signal to determine state of charge (SOC) or state of health (SOH) (or both) of the battery.

In an example, the sensor is a surface acoustic wave device. The surface acoustic wave device may be embedded in the battery and include a plurality of acoustic reflectors. The surface acoustic wave device may convert the input signal to a surface wave acoustic signal that is reflected by the plurality of acoustic reflectors to produce a reflected signal, and then may convert the reflected signal to the output signal. The control circuitry may use a change in the output signal to determine battery temperature, state of charge (SOC), or state of health (SOH) (or combinations thereof). The control circuitry may determine a phase shift between the input signal and the output signal to determine battery temperature.

The present disclosure also describes a rechargeable battery monitoring system that may comprise any of the above examples. Such a monitoring system can be used with a vehicle, such as an automobile, a hybrid electric vehicle, a mobile electronic device, a mobile communication device, and the like.

A battery state determination method is also disclosed and may include wirelessly transmitting an input signal, receiving the input signal by a passive sensor connected to a battery, outputting an output signal that changes based on a modulus of the battery, and determining battery state using the output signal.

BRIEF DESCRIPTION OF THE DRAWINGS

FIGS. 7A and 7B show a sensor according to the teachings herein that has a different sensor reading based on a physical characteristic of a battery cell.

FIG. 8 depicts a method for passive sensing of battery cells.

DETAILED DESCRIPTION

The present document details embodiments of the present invention herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
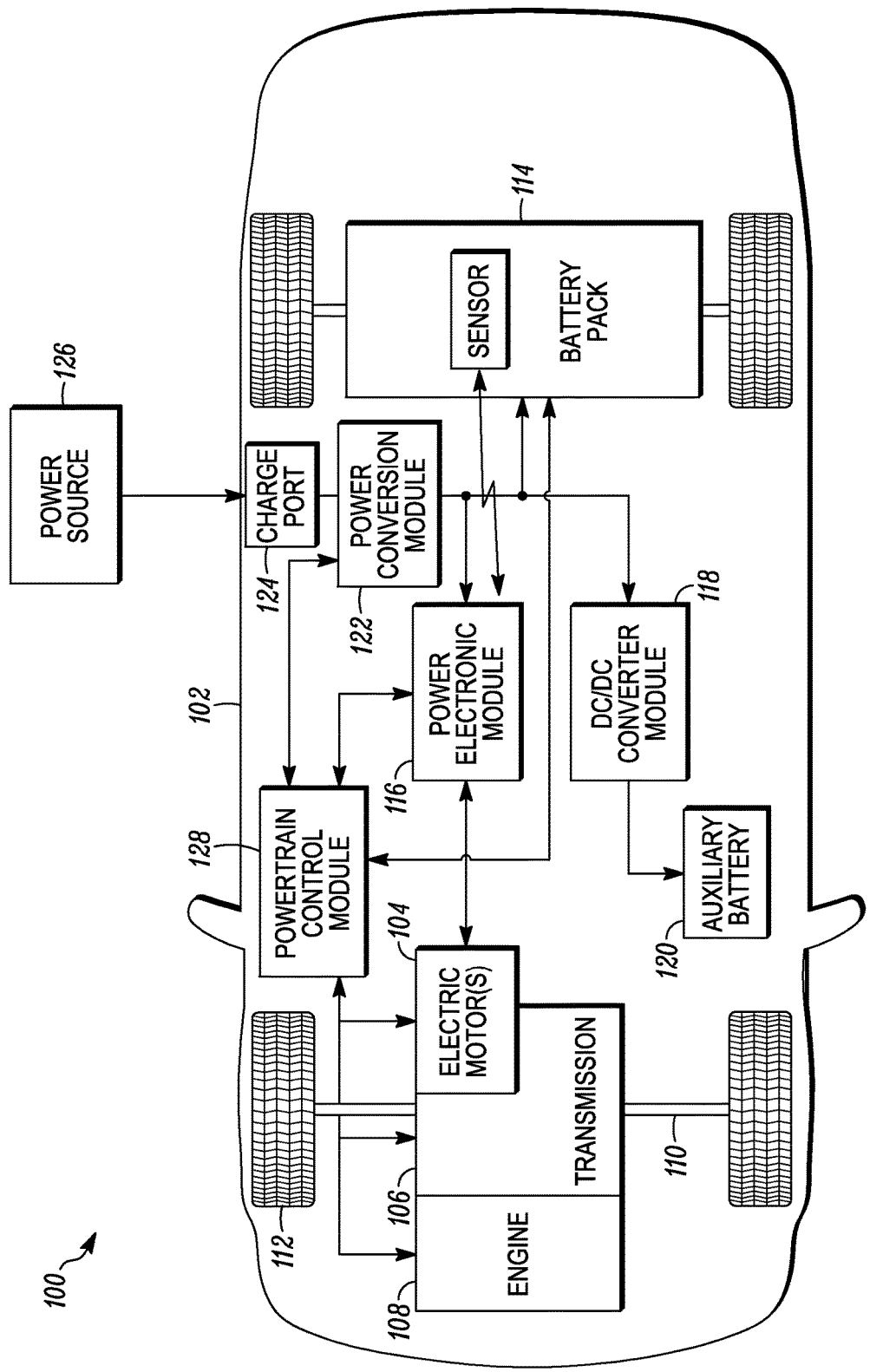
FIG. 1 is an example hybrid-electric vehicle with a battery pack.

FIG. 1 depicts an example 100 of a plug-in hybrid-electric vehicle. A plug-in hybrid-electric vehicle 102 may comprise one or more electric motors 104 mechanically connected to a hybrid transmission 106. In addition, the hybrid transmission 106 is mechanically connected to an engine 108, for example an internal combustion engine. The hybrid transmission 106 may also be mechanically connected to a drive shaft 110 that is mechanically connected to the wheels 112. The electric motors 104 can provide propulsion when the engine 108 is turned on. The electric motors 104 can provide deceleration capability when the engine 108 is turned off. The electric motors 104 may be configured as generators and can provide fuel economy benefits by recovering energy that would normally be lost as heat in the friction braking system. The electric motors 104 may also reduce pollutant emissions since the hybrid electric vehicle 102 may be operated in electric mode under certain conditions.

The traction battery or battery pack 114 stores energy that can be used by the electric motors 104. A vehicle battery pack 114 typically provides a high voltage DC output. The battery pack 114 is electrically connected to a power electronics module 116. The power electronics module 116 is also electrically connected to the electric motors 104 and provides the ability to bi-directionally transfer energy between the battery pack 114 and the electric motors 104. For example, a battery pack 114 may provide a DC voltage while the electric motors 104 may require a three-phase AC current to function. The power electronics module 116 may convert the DC voltage to a three-phase AC current as required by the electric motors 104, for example, by using an inverter module. In a regenerative mode, the power electronics module 116 will convert the three-phase AC current from the electric motors 104 acting as generators to the DC voltage required by the battery pack 114, also using an inverter module or other circuitry. The methods described herein are equally applicable to a pure electric vehicle or any other device or vehicle using a battery pack.

In addition to providing energy for propulsion, the battery pack 114 may provide energy for other vehicle electrical systems. Such a system may include a DC/DC converter module 118 that converts the high voltage DC output of the battery pack 114 to a low voltage DC supply that is compatible with other vehicle loads. Other high voltage loads, such as compressors and electric heaters, may be connected directly to the high-voltage bus from the battery pack 114. In a vehicle, the low voltage systems may be electrically connected to a 12V battery 120. An all-electric vehicle may have a similar architecture but without the engine 108.

The battery pack 114 may be recharged by an external power source 126. The external power source 126 may provide AC or DC power to the vehicle 102 by electrically connecting through a charge port 124. The charge port 124 may be any type of port configured to transfer power from the external power source 126 to the vehicle 102. The charge port 124 may be electrically connected to a power conversion module 122. The power conversion module may condition the power from the external power source 126 to provide the proper voltage and current levels to the battery pack 114. In some applications, the external power source 126 may be configured to provide the proper voltage and current levels to the battery pack 114 and the power conversion module 122 may not be necessary. The functions of the power conversion module 122 may reside in the external power source 126 in some applications. The vehicle engine, transmission, electric motors, battery, power conversion and power electronics may be controlled by a powertrain control module (PCM) 128.

The battery pack 114 can include a plurality of cells that have electrodes to electrically connect the cell to other circuitry. The battery parameters and status can be sensed by placing passive sensors in the battery pack or in each battery cell. A signal external to the battery can interrogate the sensor. In an example, the signal also energizes the sensor. The sensor can include radio frequency identification tag technology as well as battery sensing technology. The sensor then sends a sensed signal outside the battery pack to a receiver that is connected to other vehicle circuitry.

In addition to illustrating a plug-in hybrid vehicle, FIG. 1 can illustrate a battery electric vehicle (BEV) if engine 108 is removed. Likewise, FIG. 1 can illustrate a traditional hybrid electric vehicle (HEV) or a power-split hybrid electric vehicle if components 122, 124, and 126 are removed. FIG. 1 also illustrates the high voltage system which includes the electric motor(s), the power electronics module 116, the DC/DC converter module 118, the power conversion module 122, and the battery pack 114. The high voltage system and battery pack includes high voltage components including bus bars, high voltage connectors, high voltage wires, and circuit interrupt devices.

Figure 2:
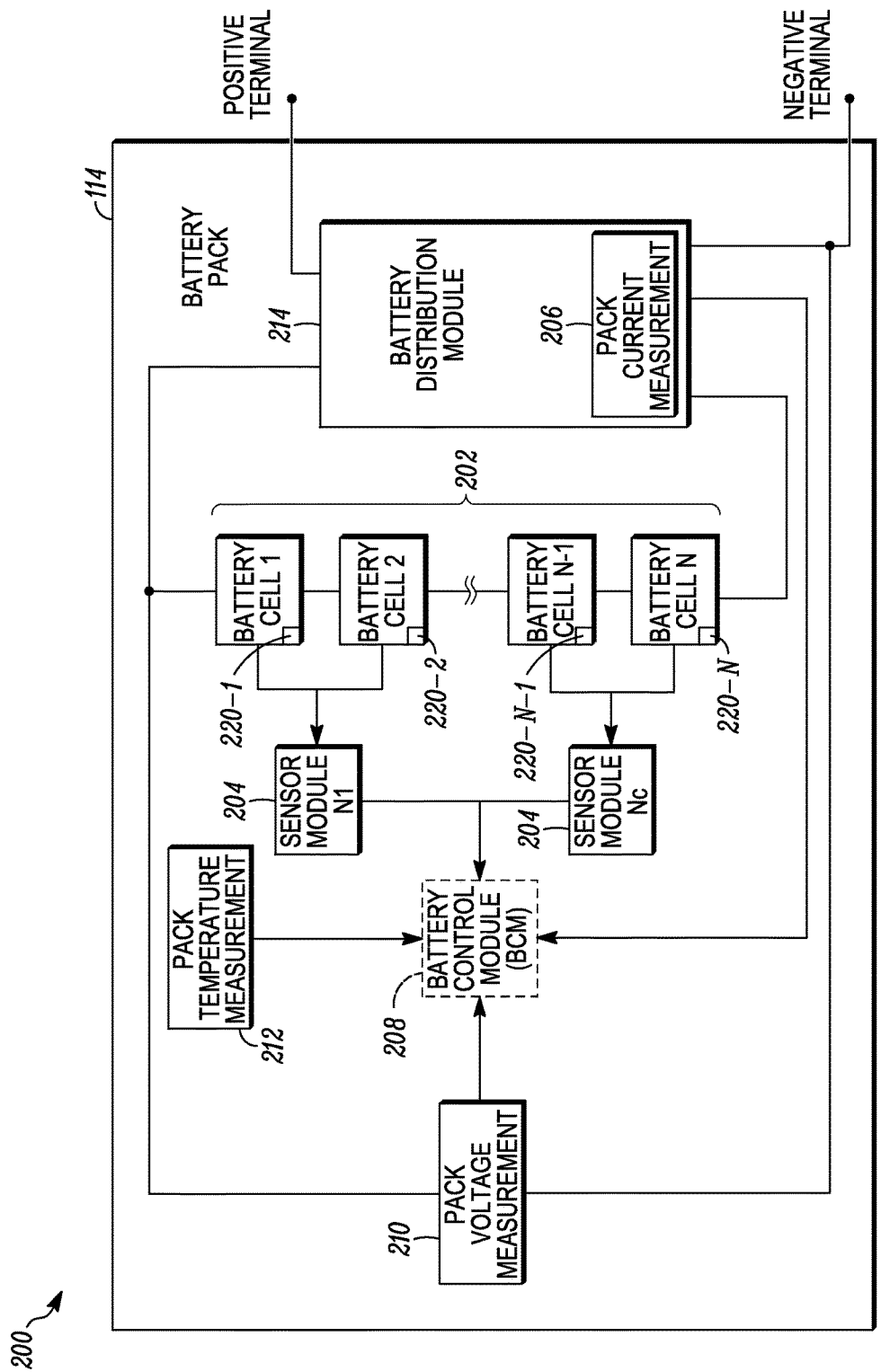
FIG. 2 is a battery pack arrangement comprised of battery cells and battery cell monitoring and controlling systems.

The individual battery cells within a battery pack can be constructed from a variety of chemical formulations. Battery pack chemistries may include, but are not limited, to lead acid, nickel cadmium (NiCd), nickel-metal hydride (NIMH), Lithium-Ion or Lithium-Ion polymer. FIG. 2 shows a battery pack 200 in a simple series configuration of N battery cell modules 202. The battery cell modules 202 may contain a single battery cell or multiple battery cells electrically connected in parallel with the connections being made at electrodes. The battery pack, however, may be composed of any number of individual battery cells and battery cell modules connected in series or parallel or some combination thereof. A system may have one or more controllers, such as a Battery Control Module (BCM) 208 that monitors and controls the performance of the battery pack 200. The BCM 208 may monitor several battery pack level characteristics such as pack current measured by a current sensor 206, pack voltage 210 and pack temperature 212. The performance of the current sensor 206 may be essential, in certain arrangements, to build a reliable battery monitoring system. The accuracy of the current sensor may be useful to estimate the battery state of charge and capacity. A current sensor may utilize a variety of methods based on physical principles to detect the current including a Hall Effect IC sensor, a transformer or current clamp, a resistor in which the voltage is directly proportional to the current through it, fiber optics using an interferometer to measure the phase change in the light produced by a magnetic field, or a Rogowski coil. In the event a battery cell is charging or discharging such that the current entering or exiting the battery cell exceeds a threshold, the battery control module may disconnect the battery cell via the use of a circuit interrupt device (CID) such as a fuse or circuit breaker.

The battery cell may exhibit physical changes, such as swelling and contraction (which changes the cell's Young's modulus), as state of charge changes. In the case of a lithium (Li) ion battery including an electrode made of metal oxides and Li ions, Li is inserted into and de-inserted from the electrode during discharging and charging, respectively. This process induces micro-structural changes (swelling and contraction), thus changing the modulus (a material property) of the electrode. For example, the modulus of graphite increases with lithium insertion. Young's Modulus for a graphite electrode changes by nearly a factor of 3 when full of Li. The change in modulus can be measured according to the systems and methods described herein, e.g., a sensor at or within the battery cell or battery pack.

In addition to the pack level characteristics, there may be battery cell level characteristics that need to be measured and monitored. For example, the terminal voltage, current, and temperature of each cell or a representative subset of cells may be measured. A system may use a sensor module 204 to measure the characteristics of one or more battery cell modules 202. The characteristics may include battery cell voltage, temperature, age, number of charge/discharge cycles, etc. In an example, a sensor module 204 will measure battery cell voltage. Battery cell voltage may be voltage of a single battery or of a group of batteries electrically connected in parallel or in series. The battery pack 114 may utilize up to $N_c$ sensor modules 204 to measure the characteristics of a representative sample or all of the battery cells 202. The sensor modules 204 may communicate battery cell sensors 220. Battery cell sensors 220-1, 220-2, . . . 220-N-1 and 220-N are fixed to each battery cell 1, 2, N-1, N. The battery cell sensors can be passive sensors, e.g., radio frequency identification tags, surface acoustic wave sensors, or other similar sensors, that are integral with the battery cell structure. The battery cell sensors 220 can sense a physical property of the battery cell and produce an output signal that can be received by the sensor module 204 in response to the measured battery cell physical property. Each sensor module 204 may transfer the measurements to the BCM 208 for further processing and coordination. The sensor module 204 may transfer signals in analog or digital form to the BCM 208. The battery pack 114 may also contain a battery distribution module (BDM) 214 which controls the flow of current into and out of the battery pack 114.

Figure 3:
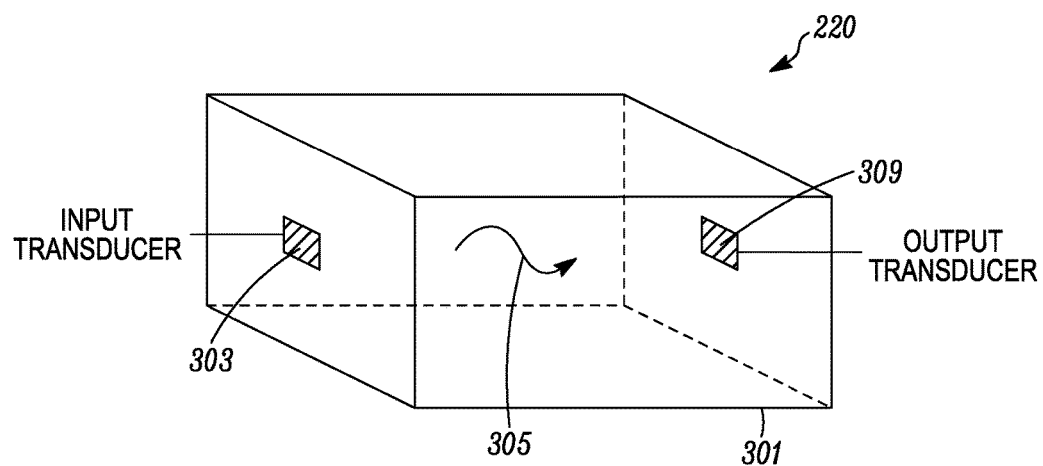
FIG. 3 is a schematic view of a battery cell with a passive sensor and reader, in an example.

FIG. 3 shows a schematic view of a sensor 220 for a battery cell 301. The sensor 220 includes a signal input device 303 (e.g., a transducer) that inputs a test signal 305 at one end of the battery cell 301. The test signal 305 is a physical wave or propagating wave that travels in the battery cell 301. The structure and media of the battery cell 301 modifies or alters the test signal 305 while it travels through the battery cell. The modified signal is received by at least one output device 309 (e.g., a transducer). The output device 309 is positioned at an opposite end of the battery cell 301 in the illustrated example of FIG. 3. If there are multiple output devices 309, then these can be positioned at the same end of the battery cell 301 as the illustrated example or can be positioned at different sides of the battery cell. The output device 309 converts the propagating wave into a signal that can be wirelessly transmitted to the sensor module 204 (see, e.g., FIG. 2). The output device 309 can send the signal directly to the sensor module or can modify or interpret the received signal and send the result to the sensor module. In the case of batteries for electric vehicles, the test signal propagating through the battery cell may change in velocity, phase, amplitude and/or loss, as the modulus changes, which may dependent on the charge of the battery cell. This change may be directly related to the SOC and state of health (SOH) of the battery or battery cell.

Test signal 305 of the sensor 220 should be chosen to meet the requirement of propagation through the battery. The test signal 305 should not be completely absorbed or stopped by the battery cell 301. The signal 305 should be able to penetrate the battery cell casing, which can be a polymer or a metal, such as aluminum. Certain short waves may not be suitable for a test signal 305, e.g., short waves like infrared, visible light and ultraviolet are too dense to pass through a battery. Radio wave lengths are long waves and thus can pass through a battery. Additionally the test signal 305 should not be completely absorbed by the electrolyte in the battery. In an example, microwaves may be used as the test signal as they are less sensitive to electromagnetic interference.

Figure 4:
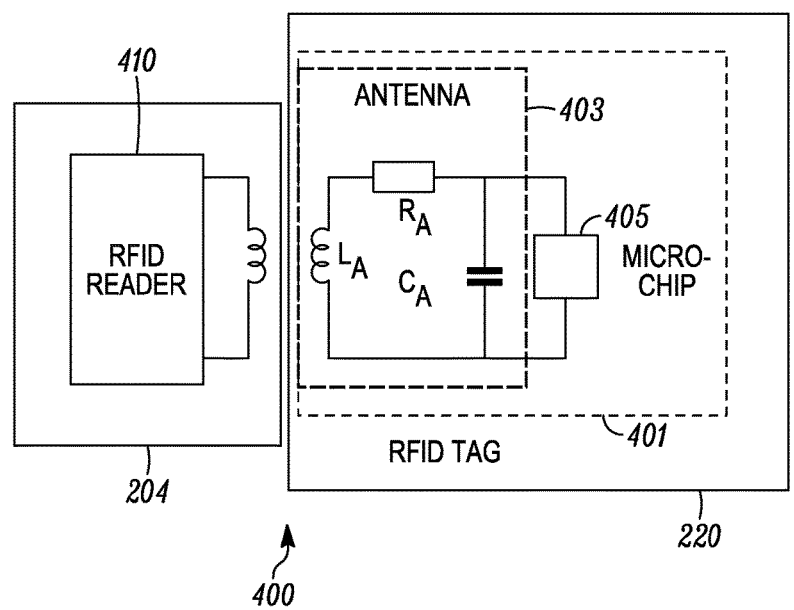
FIG. 4 shows a schematic view of a sensor for a battery cell.

FIG. 4 shows a passive, wireless sensing system 400 that can include the sensor module 204 and a battery cell sensor 220, which as described herein is fixed or integral with the battery cell. The battery cell sensor 220 can include a radio frequency identification (RFID) tag 401 that consists of an antenna 403 and an integrated circuit 405, e.g., s micro-chip. The antenna 403 is used to communicate information stored in memory on an integrated circuit device, e.g., a micro-chip. The RFID tag 401 can be a passive tag, semi-passive tag, or active tag. Active and semi-active tags both have an external power source used to power the tag and/or the micro-chip. In this case the power can be from the battery cell itself. Passive tags have no on-board power source. These have the benefit of being easier to fabricate and to fix to the battery cell. Passive tags can also be less expensive. A passive tag is powered through an external electric field that is coupled with the antenna. The energy transferred to the tag is used to turn the circuitry on, releasing the identification number encoded on the chip and perform any measurements. This information is sent back to the external source, identified as the sensor module, e.g., an RFID reader 410. By implementing an RFID sensor into a full RFID system, including the tag and external reader, the present system has the potential to have a wireless sensor, adding further improvements over current battery sensors. The antenna 403 is shown as a simple RLC circuit dependent on the geometry of the antenna coil.

Figure 5:
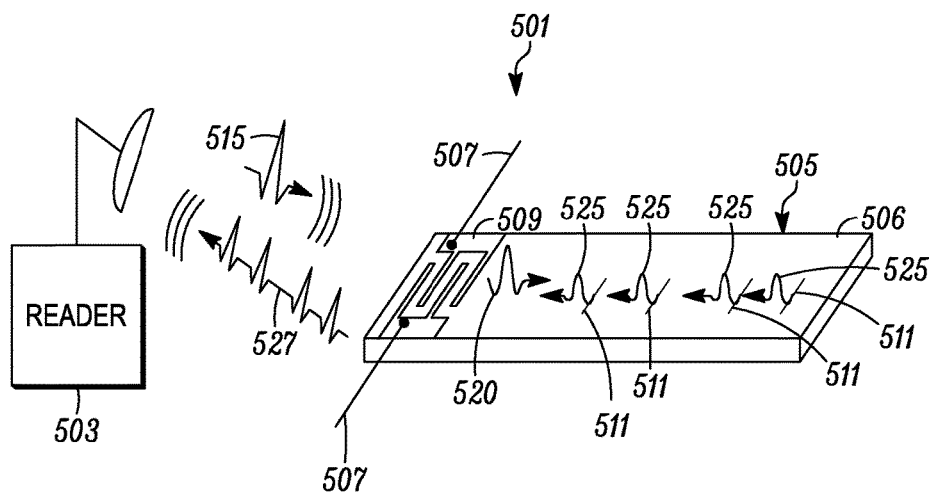
FIG. 5 is a view of a surface acoustic wave sensor for use with a battery cell, in an example.

FIG. 5 shows a surface acoustic wave (SAW) sensor system 501 for a battery cell. The system 501 can be used in a mobile apparatus, e.g., a vehicle or communication device. The SAW sensor system 501 includes a transmitter/receiver 503 that sends and receives signals in the form of radio signals. While described as a transmitter/receiver, it is within the scope of the present disclosure to physically separate these two parts and have a separate transmitter that is separate from the receiver. The SAW sensor 505 includes a body 506 in which an antenna 507 is embedded and on which a transducer 509 and a plurality of wave reflectors 511 are formed. The body is a piezoelectric crystal or material that is excitable by RF signals and similarly changes shape based on applied strain caused by external factors or the environment. In operation, the transmitter/receiver 503 wirelessly sends and receives digital signals. The sent signal 515 can operate as an interrogation signal and power the SAW sensor 505. The sent signal 515 is wirelessly received at the antenna 507, which in turn feeds the transducer 509. The transducer 509 can be an interdigital transducer. The transducer 509 converts the received signal into a wave 520, e.g., surface wave acoustic pulses, that propagates in the body 506. The wave 520 impinges on at least some of the wave reflectors 511, which reflect the wave back 525 to the transducer 509. The transducer 509 converts the reflected wave to electrical signals and wirelessly transmits a return signal 527 to the transmitter/receiver 503. The differences in the electrical signal(s) sent to the SAW sensor 505 and those received from the SAW sensor indicate a physical characteristic of the battery cell. The signal sent by the transmitter/receiver 503 can be generated by the sensor module 204, the battery control module 208 or other circuitry in the vehicle. Likewise, the signal received from the transmitter/receiver 503 can be processed by the sensor module 204, the battery control module 208 or other circuitry in the vehicle to determine the physical characteristic of the battery cell.

As surface acoustic wave (SAW) devices are sensitive to temperature, pressure, stress, liquid viscosity, and surface effects, a range of sensors are possible for a battery cell. The present inventors have recognized that an array of sensors can be positioned in, fixed to or fabricated within a battery cell in which each sensor responds to a different measurement. It is further recognized that a battery cell internal environment can be quite caustic. Nonetheless, the sensors could be embedded within the casing of the battery cell and would be in intimate contact with the electrode of the battery cell. Additionally, sensors can be packaged to withstand the internal environment of the battery cell. The sensors would be powered by the signal transmitted by the reader/interrogator and each send a reply signal to the post processor, e.g., any circuitry or module in the vehicle. The substrate of the SAW device can change in a mechanical or physical way in response to changes in the battery environment. As a result, the reflectors move relative to one another and the reflected signal and the return signal differ from other signals based on the state of the substrate and position of the reflector(s).

Figure 6:
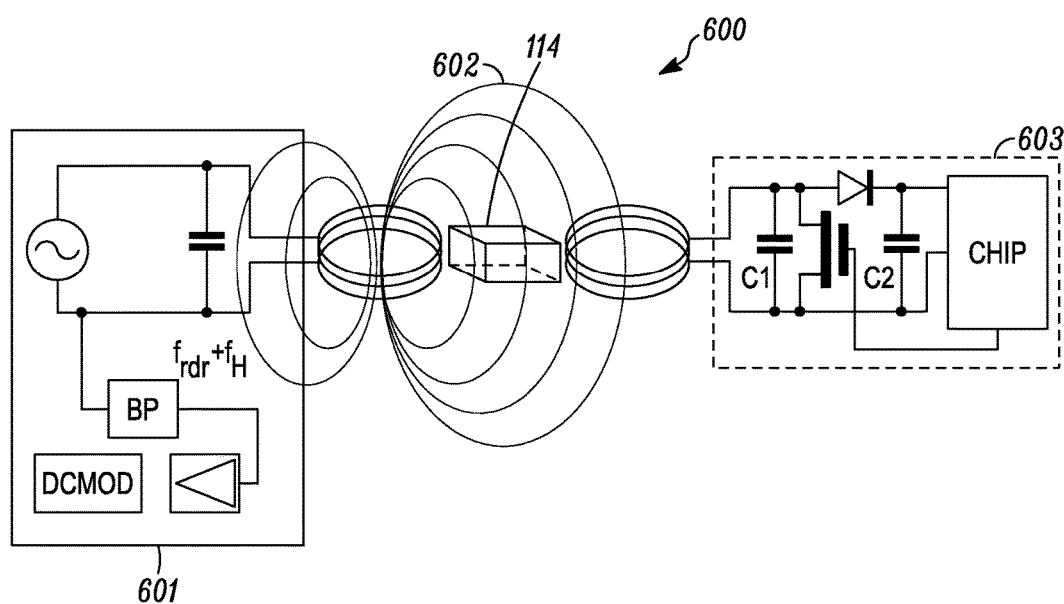
FIG. 6 is a view of a passive sensor for use with a battery cell, in an example.

FIG. 6 shows magnetic sensor system 600 for use with a battery cell 220. The sensor system 600 includes a transmitter 601 that emits a signal 602 that is affected by the battery cell and received at a sensor 603, which can be a radio frequency identification tag. The difference in the signal received at the sensor 603 compared to the signal emitted by the transmitter 601 can be interpreted to represent the status of the battery pack 114 or battery cell(s) 220 or components of the battery, e.g., electrodes, chemical structure, state of charge, state of health, etc. In this example transmitter 601 emits a magnetic field H signal 602 from its antenna. The magnetic field H travels through at least one battery cell 220. The magnetic field H is modified by the battery cell 220. This modified magnetic field is received at an antenna of the sensor 603. In an example, the sensor 603 is powered by the received signal and includes circuitry to send an output signal based on the received magnetic signal to the transmitter 601 or to the sensing module 204. Either the sensing module 204 (or other vehicle circuitry) or transmitter 601 can compare the output signal to the transmitted signal or stored possible output signals to determine a physical characteristic of the battery cell. In an example, the vehicle's on-board circuitry or processing modules, e.g., power electronics module 116 can process, compare or interpret the received signals. When the field between the transmitter 601 and sensor 603 is perturbed by the changing modulus of the electrode material of the battery, a shift in the signal of the sensor can be measured. This shift will be directly correlated to the SOC and state of health of the cell/battery.

FIGS. 7A and 7B show sensor 701 according to the teachings herein that has a different sensor than that shown in FIG. 6 for reading a physical characteristic of a battery cell. Sensor 701 is adjacent the battery cell 220. Sensor 701 can sense a signal 705 (705' in FIG. 7B) to determine the characteristic of the battery. The sensor 701 can be a tunneling magnetoresistance (TMR) device with two magnetic layers (e.g., ferromagnets such as CoFeB) separated by a thin insulator (e.g., MgO that is a few atoms thick) that can emit and sense a magnetic field. A TMR device uses a quantum mechanical process to read the magnetic field through a process called tunneling. A biasing voltage is created between the metals, by allowing current to flow across the insulator. The likelihood of quantum tunneling is directly related to electron spin alignment, which can be manipulated and controlled by introducing external magnetic fields, with the following consequence: as the strength of the magnetic field increases, the electron spin alignment increases, and more electrons may tunnel across the insulator. As more electrons tunnel across the insulator, the resistance of the device falls. Accordingly, the magneto resistance of the sensor is the first indication of its performance: for example, anisotropic sensors have 2-3% magneto resistance, whereas giant sensors have 15-20% magneto resistance. By contrast, sensors that implement magnetic tunnel junctions have a magneto resistance of 200%.

In an example, the sensor 701 is positioned adjacent an electrode 706 of the battery within a battery housing 707. A physical characteristic of the electrode 706 at a first state results in a first signal field 705. A change in the physical characteristic of the electrode 706 at a second state results in a second signal field 705'. In an example, the electrode 706 includes battery anode materials for lithium (Li) ion batteries and includes metal oxides and Li ions which can readily be inserted and withdrawn from the oxides. Li is a paramagnetic material and hence anode magnetic properties (i.e., magnetic susceptibility) changes during charge and discharge cycles. In the presence of a magnetic field 705, the anode becomes magnetized. The magnetic field 705 for a fully charged battery can be sensed and used as a baseline (FIG. 7A). As the battery discharges, the magnetic field 705' will be perturbed and will directly measure the state of charge (SOC) of the battery as shown in FIG. 7B. FIG. 7A shows a magnetic field 705 response of a battery that is 100% SOC. FIG. 7B shows a magnetic field 705' response of a battery that is 20% SOC. A battery with a lower charge has a measurable increase in magnetic susceptibility and hence there is a greater magnetic field compared to batteries with greater charge states. In the present example, the battery electrode for a battery with 20% state of charge has a three-fold increase in magnetic susceptibility compared to one that is fully charged.

While the above example describes lithium ion batteries, this technique may be used for sensing other battery types, e.g., lead acid batteries and lithium iron phosphate batteries.

The sensor 701 can be a passive sensor that does not need to emit a signal and it senses the magnetic field of the battery electrode. The change in the sensed magnetic field can indicate change in a physical characteristic of the battery.

FIG. 8 shows a method 800 for passive sensing of physical characteristics of battery cells. This method can be used with the systems described herein. At 801, a sensor component is fixed to or within the battery or cell of the battery. The sensor component can communicate wirelessly and can be a passive device. At 803, a test signal and/or a power signal is wirelessly sent to the sensor component, which can travel through the battery. At 805, the signal that travels through the battery is sensed. This sensed signal is affected by the battery. At 807, the battery state or a physical characteristic of the battery is determined. Electronic circuitry can operate to determine the change in sensed signal versus what is sent into the battery.

Figure 9:
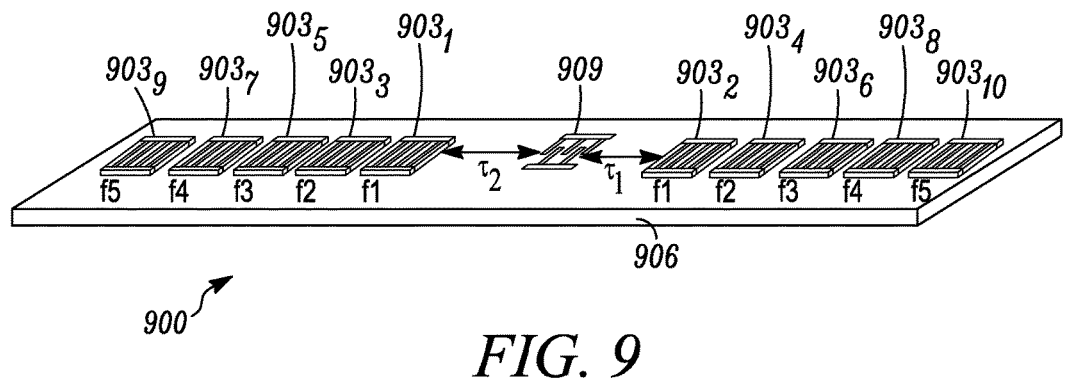
FIGS. 9 through 12 show schematic views of sensors for batteries.

FIG. 9 shows a schematic view of a sensor 900 for a battery or battery cell. The sensor 900 is a surface acoustic wave device with a one-port dual delay, orthogonal frequency coding (OFC) with multiple chips on the substrate 906. The substrate 906 can be made from piezoelectric crystals such as YZ $LiNbO_3$. Here there is shown five chips per OFC bank ($903_1$-$903_{10}$) for a total of ten chips. Each can be assigned to a different center frequency that meets the orthogonality condition. The chips are then activated by a specific input signal modulated by the signal from transducer 909. In another example, the even bank of five multiple chips (right side of transducer 909) is activated by the signal $t_1$. The odd bank of multiple chips (left side of transducer 909) is activated by the signal $t_2$. The chips can be shuffled in time, due to the position of the chips, to produce a unique code returning from the sensor 900. This structure allows both frequency and pseudo noise (PN) coding. Additionally, the interrogation signal can be increased in power relative to a single chip. This allows for a hybridization of orthogonal frequency division multiplexing (OFDM) and binary phase shift keying (BPSK) coding techniques. Each bank of chips is set at a sequence of reflectors with center frequencies from $f_1$ to $f_5$. The time lengths and frequencies of each reflector are chosen such that the peaks of each chip lines up with the nulls of all other chips. The orthogonality condition states that $$N_j = \tau_c f_j \tag{1}$$

where $N_j$ is the number of reflector electrodes, $\tau_c$ is the chip length (i.e., time length of each chip), and $f_j$ is the chip frequency. Once a set of frequencies is set for the chips, the frequencies can be shuffled in time to produce a unique code. Depending on the number of chips ($N_c$) and the use of PN coding, $2^{N_c} N_c!$ codes are possible. Accordingly, each sensor 900 can have a unique identifying code associated with the data returned in the returned signal.

Figure 10:
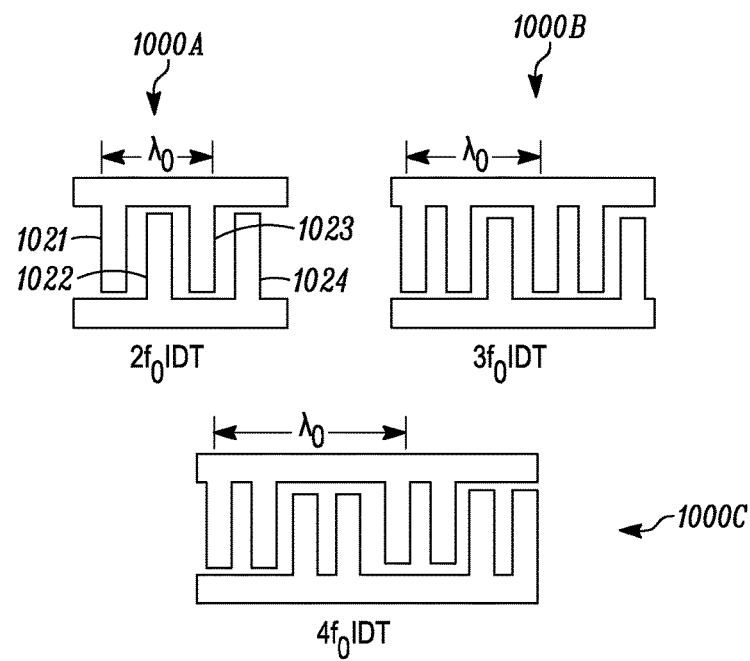

FIG. 10 shows a schematic view of interdigitated transducers 1000A, 1000B, and 1000C for a battery sensor. Each of the transducers 1000A, 1000B, and 1000C include a plurality of electrodes of opposite polarity that overlap and are separated by a dielectric layer. These transducers 1000A, 1000B and 1000C can be placed on a substrate of a SAW. Transducer 1000A includes a first electrode 1021 followed by a second electrode 1022, which are separated by a dielectric material. A third electrode 1023 follows the second electrode 1022, which are separated by a dielectric material. A fourth electrode 1024 follows the third electrode 1023, which are separated by a dielectric material. The first and third electrodes are electrically and physically connected. The second and fourth electrodes are electrically and physically connected. The transducer 1000B is similar to transducer 1000A, but the first and third electrodes have two legs. The transducer 1000C is similar to transducers 1000A and 1000B, but the first and third electrodes have two legs as does the second and fourth electrodes. The legs are also separated by a dielectric. Transducers 1000A, 1000B, and 1000C are capacitive in nature. Due to the finite resistance of the electrodes, the transducers also possess a series resistance. The electrode structure may be designed for $2f_0$ (two electrode and two spaces per wavelength, $f_s=2f_0$ is the sampling frequency, 1000A), $3f_0$ (three electrodes and three spaces per wavelength, 1000B), and $4f_0$ (four electrodes and four spaces per wavelength, 1000C). The transducers 1000B and 1000C ($3f_0$ and $4f_0$) are split electrode transducers and can act to minimize internal reflections (since energy gets trapped in the transducer) and bulk mode conversion, especially in delay line devices. For devices with equal electrode width and space, the electrode width is $\lambda/4$, $\lambda/6$, and $\lambda/8$ for $2f_0$, $3f_0$, and $4f_0$, respectively; where $f_0$ is the fundamental frequency.

Figure 11:
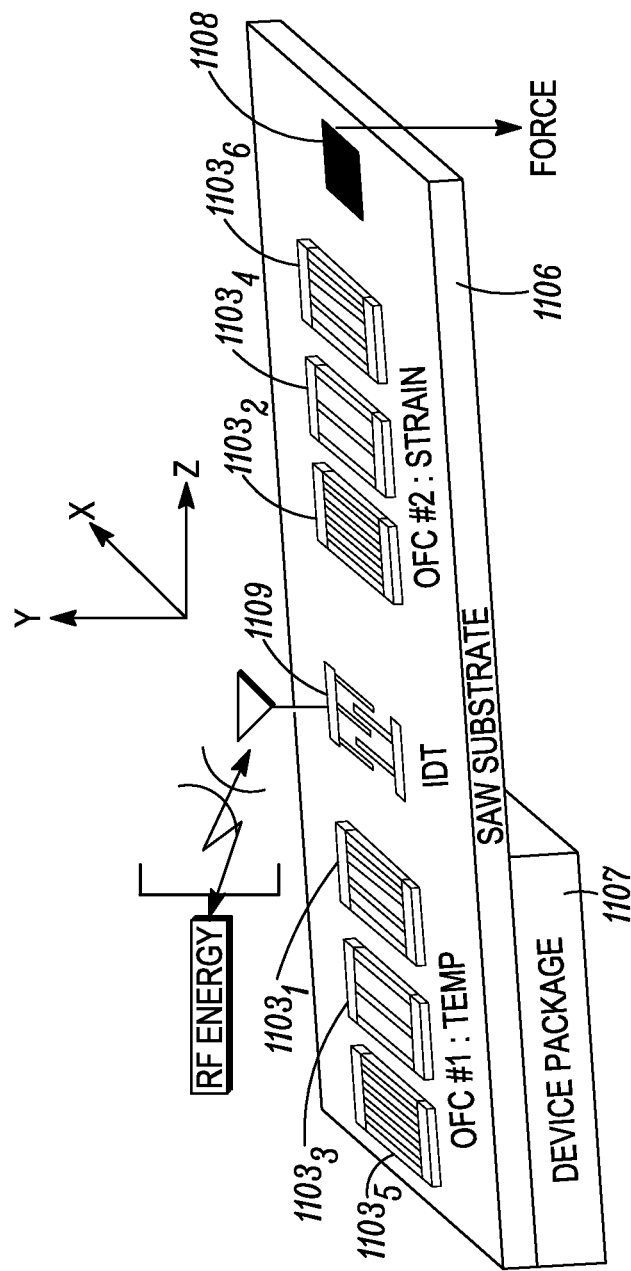

FIG. 11 shows a schematic view of a sensor 1100 for a battery or battery cell. The sensor can be a surface wave acoustic sensor. The sensor 1100 can include a one-port dual delay, orthogonal frequency coding (OFC) with multiple chips on the substrate 1106. Other wireless coding can be used to send information and energy signals to the sensor 1100. A device package 1107 supports the substrate 1106 at one end portion such that the other end is cantilevered and can deflect. The deflection movement can be sensed and the resulting data can represent the battery states or other battery information. The substrate 1106 can be a YZ LiNbO$_3$ structure in an example. In FIG. 11, there is shown three chips per OFC bank ($1103_1$-$1103_6$) for a total of six chips in two banks on opposite sides of the transducer 1109. The chips $1103_1$-$1103_6$ can be surface acoustic wave acoustic devices that receive a surface wave from the transducer 1109 and return a signal to the transducer 1109 indicating information relating to the battery. The battery can place a strain on the saw substrate 1106 that is sensed by the signal to/from the chips $1103_1$-$1103_6$. The bank of chips $1103_1$, $1103_3$, and $1103_5$ are positioned at the end portion of the substrate that is directly supported by the package 1107. Chips $1103_1$, $1103_3$, and $1103_5$ can measure the temperature at the battery, either in the battery adjacent the internal battery chemistry or on the battery package or case. Chips $1103_1$, $1103_3$, and $1103_5$ can also provide a non-strained or displaced baseline signal, which can be used when determining strain or displacement at the other end of the sensor 1100. The second bank of chips $1103_2$, $1103_4$, and $1103_6$ are positioned at the end portion of the substrate that is not directly supported by the package 1107. The second bank of chips $1103_2$, $1103_4$, and $1103_6$ are an end of the substrate 1106 that is the free end of the cantilevered substrate. Chips $1103_2$, $1103_4$, and $1103_6$ can measure the strain experienced by the substrate, either in the battery adjacent the internal battery chemistry or on the battery package or case. In an example, the strain can be caused by a magnet 1108 positioned at the free end of the cantilevered substrate. The magnet 1108 produces a magnetic field and senses changes in the battery via the electromagnetic fields in the battery. In an example, the magnet 1108 senses the magnetic field in the adjacent region of the vehicle battery. As the magnet 1108 electromagnetically interacts with the magnetic field of the battery, the substrate is moved and its displacement can be sensed by the chips $1103_2$, $1103_4$, and $1103_6$. While described herein as chips, the chips $1103_1$-$1103_6$ can include electronic structures, MEMS structures or combinations thereof. The sensor 1100 can include the interdigitated transducers as described with regard to FIG. 10.

Figure 12:
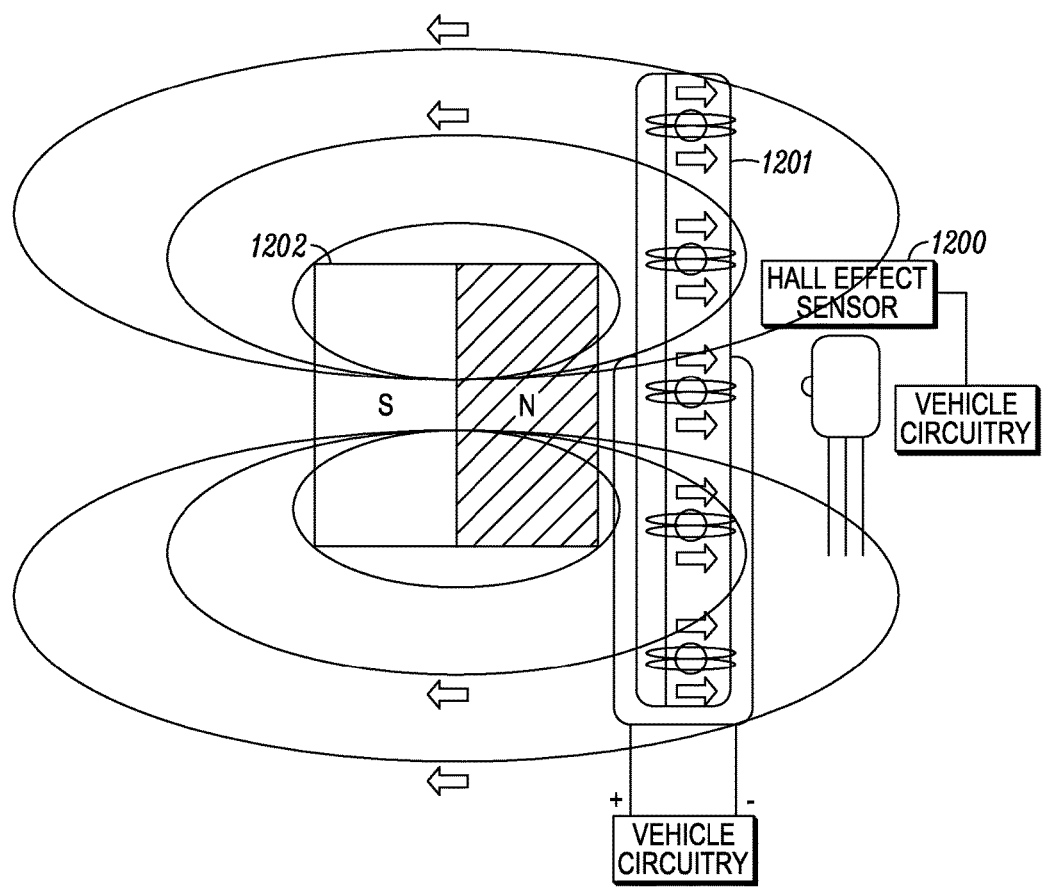

FIG. 12 shows another sensor 1200 that can be used with a battery or battery cell 1201 for a vehicle. A permanent magnet 1202 can be positioned at or adjacent a battery 1201. The magnet 1202 produces a steady-state magnetic field. The magnetic field extends into the battery 1201. The battery 1201 changes the magnetic field based on its physical state. This magnetic field change can be sensed by the sensor 1200. When a paramagnetic material, e.g., Co or Ni, in the battery are placed in the magnetic field, they align themselves such that their magnetic dipole opposes the incident magnetic field. Since the field at the sensor is the sum of these fields, the field at the sensor 1200 is reduced. The sensor 1200 can be a Hall Effect sensor or other magnetic field sensor, which may output a voltage in response to a sensed magnetic field. In an example as the battery 1201 is cycled through charging and discharging, transition metals within the battery are changing oxidation states. The change in oxidation state may be greatest at the battery cathode. As a result, the magnetic susceptibility of the battery, i.e., the cathode, will change in the intensity of the magnetic field. In operation, the magnetic field from magnet 1201 is constant but the state of the battery 1201 will affect the magnetic field sensed by the sensor 1200 in response to changes in the battery, e.g., cathode magnetic susceptibility.

Figure 13:
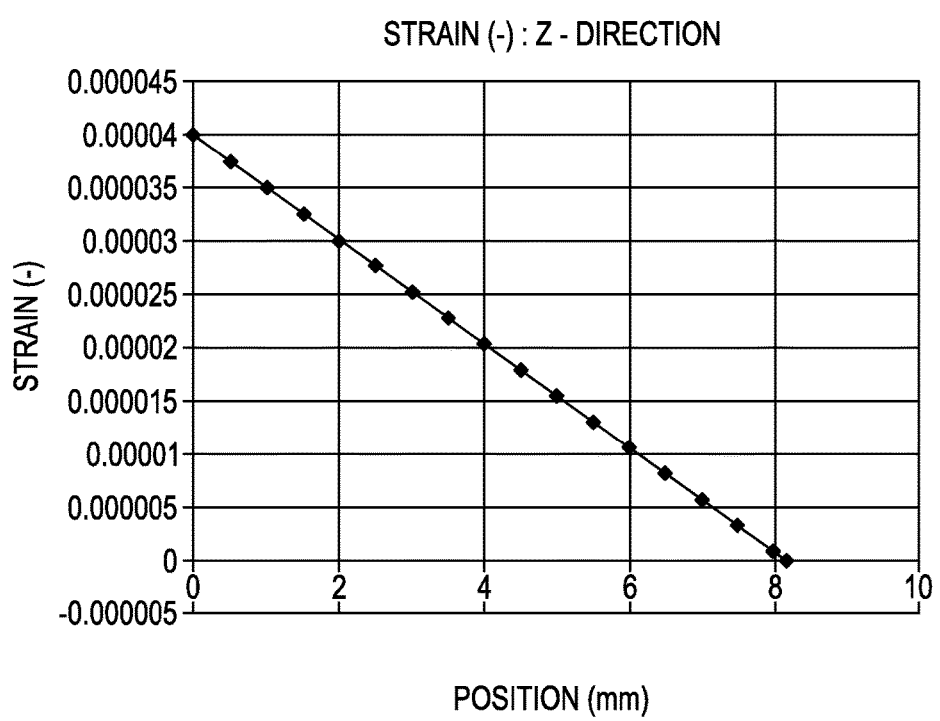
FIG. 13 shows a graph of strain and position for a battery sensor.

FIG. 13 shows an example of strain on a sensor, e.g., the sensor shown in FIGS. 5 and 9-11. As an example, the sensor receives a strain of about 0.05N as a downward force on the end (or tip) of the substrate of the sensor. This strain can be sensed by the sensor and sent to other circuitry in the vehicle to be used in determining the battery state, which in turn can be used to control electrical operation of the battery systems in the vehicle.

Figure 14:
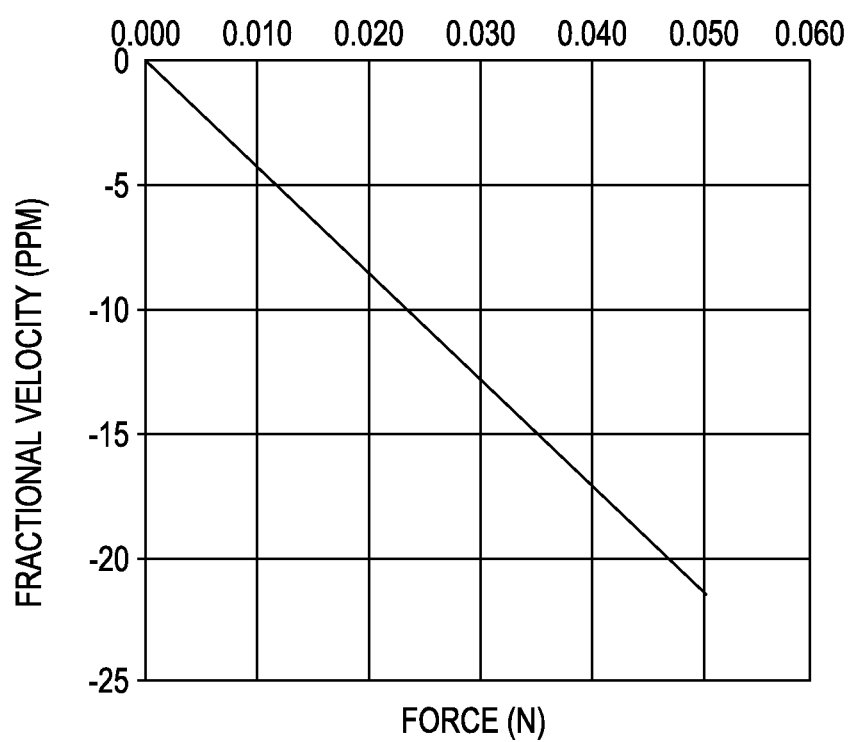
FIG. 14 shows a graph of fractional velocity versus force at a battery sensor.

FIG. 14 shows an example of fractional velocity experienced by the sensor, e.g., the sensor shown in FIGS. 5 and 9-11 versus the force experienced by the sensor. The fractional velocity change is in parts per million. The strain on the sensor, e.g., a cantilevered sensor substrate can be at a position 6 mm from the supported fixed part of the sensor. By appropriately designing the center frequency ($f_0$) for the sensor, a very sensitive sensor can be developed.

The systems and methods described herein can measure temperature at and within each battery cell and state of charge. Specifically, using smart sensor systems that can be embedded with the battery cell direct measurement of the physical characteristics or internal state of the battery cell can provide more precise knowledge of the operating state of the battery cell. This knowledge can be used in control techniques for the battery cell and vehicle. The use of passive sensors with wireless communication allows the direct measurement of battery cell characteristics, which heretofore was not possible. As these direct measurements were not done, control algorithms made assumptions that may not be accurate or may operate in an inefficient manner. These direct measurements can be used on their own or in combination with cell voltage measurement techniques.

The sensors and tags described herein are packaged to withstand the vehicle environment. The vehicle environment includes the temperature and moisture as well as the vibrations associated with vehicle travel and engine vibrations. The sensors and tags if mounted to or within the battery are further packaged to withstand the temperature range −40° C. to 75° C. (storage: 85° C.) and possible caustic environment of batteries. The sensors can communicate wirelessly with other communication devices within the vehicle or with paired components. The sensor systems described herein can observe the internal states of the battery and use this information to determine information, e.g., voltage, SOC, localized temperature, state of health, etc. These sensor systems are believed to be low maintenance compared to current sensors as they do not have batteries or other power sources to be replaced or replenished or connected. These sensors have a small size, on the order of a grain of rice in some instance, and hence ensure unobtrusive deployment either on the battery or in the battery. It is believed that these sensors may facilitate the deployment of multiple sensors to form a distributed wireless sensor network as well as maintain electromagnetic compliance with the vehicle as these devices are low power with small electromagnetic fields.

The present disclosure uses the term chips, which can be circuitry, integrated circuits, packaged circuits, micro-electro-mechanical systems (MEMS) or combinations thereof that can perform the functions described herein. The chips, in various examples, may have to meet the environmental extremes of internal battery conditions, battery packaging, or mounting in a vehicle that is subject to high heat and freezing conditions and remain operable.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A vehicle comprising:
a battery storing electrical energy for an electric motor;
a tunneling magnetoresistance sensor connected to the battery, configured to receive a response signal from a surface-acoustic-wave sensor sensing strain at an anode of the battery representing ions thereat via tunneling magnetoresistance, and to wirelessly transmit an output signal indicating battery state using the response signal; and
control circuitry configured to control the electric motor and the battery based on the output signal.

2. The vehicle of claim 1, wherein the sensor includes a passive radio frequency identification tag.

3. The vehicle of claim 2, wherein the battery includes an electrode having a Young's modulus that changes based on the battery state and wherein the response signal is influenced by the Young's modulus.

4. The vehicle of claim 3, wherein the battery state is state of charge (SOC) or state of health (SOH) based on the sensed ions at the battery anode.

5. The vehicle of claim 1, wherein the sensor is embedded in the battery and senses changes in magnetic susceptibility of the anode of the battery relative to a baseline of a fully charges battery.

6. The vehicle of claim 1, wherein the surface-acoustic-wave sensor includes a plurality of acoustic reflectors, and is further configured to convert an input signal to a surface wave acoustic signal that is reflected by the reflectors to produce the response signal; wherein the battery state is state of charge (SOC) or state of health (SOH) based on the sensed ions at the battery anode; and wherein the sensor is embedded in the battery and senses changes in magnetic susceptibility of the anode of the battery relative to a baseline of a fully charges battery.

7. The vehicle of claim 6, wherein the state is temperature of the battery and wherein the output signal is further based on a phase shift associated with the response signal.

8. The vehicle of claim 1, wherein the sensor includes a magnet to produce a magnetic field that is dampened by a higher battery state of charge relative to a lower state of charge.

9. The vehicle of claim 8, wherein the sensor includes a hall effect sensor positioned remote from the magnet and that senses a change in the magnetic field produced by the battery.

10. A method for detecting state of a battery comprising:
wirelessly transmitting an input signal to the battery;
receiving the input signal at a passive sensor connected to the battery;
emitting a magnetic field at an electrode of the battery;
sensing battery state using a tunneling magnetoresistance sensor in the magnetic field to sense permeability of a battery electrode;
outputting a response signal that changes based on sensed permeability of the battery electrode; and
outputting battery state based on the response signal,
wherein the input signal includes an electromagnetic signal and the sensor is a surface wave acoustic sensor that senses strain at an electrode of the battery, and wherein outputting the response signal includes wirelessly outputting the response signal from the surface wave acoustic sensor to a receiver outside the battery.

11. The method of claim 10, wherein the input signal is a magnetic field.

* * * * *